US009408996B2

(12) United States Patent
Pompilio, III et al.

(10) Patent No.: US 9,408,996 B2
(45) Date of Patent: Aug. 9, 2016

(54) TIME-DRIVEN PERSONALIZATION OF MEDIA PREFERENCE

(71) Applicant: SimpleC, LLC, Atlanta, GA (US)

(72) Inventors: Daniel V. Pompilio, III, Smyrna, GA (US); Jason Zamer, Atlanta, GA (US)

(73) Assignee: SIMPLEC, LLC, Atlanta, GA (US)

( * ) Notice: Subject to any disclaimer, the term of this patent is extended or adjusted under 35 U.S.C. 154(b) by 283 days.

(21) Appl. No.: 13/709,432

(22) Filed: Dec. 10, 2012

(65) Prior Publication Data

US 2013/0150660 A1    Jun. 13, 2013

Related U.S. Application Data

(60) Provisional application No. 61/568,988, filed on Dec. 9, 2011.

(51) Int. Cl.
*A61M 21/00*    (2006.01)
*A61M 21/02*    (2006.01)
*G06F 19/00*    (2011.01)

(52) U.S. Cl.
CPC .............. *A61M 21/02* (2013.01); *A61M 21/00* (2013.01); *A61M 2021/005* (2013.01); *A61M 2021/0027* (2013.01); *A61M 2205/3553* (2013.01); *A61M 2205/3584* (2013.01); *A61M 2205/50* (2013.01); *G06F 19/3481* (2013.01)

(58) Field of Classification Search
CPC . A61M 21/02; A61M 21/00; A61M 2205/50; A61M 2021/005; A61M 2205/3553; A61M 2205/3584; A61M 2021/0027; G06F 19/34
USPC ................ 600/26–28; 128/897–899; 705/2, 3
See application file for complete search history.

(56) References Cited

U.S. PATENT DOCUMENTS

| | | | |
|---|---|---|---|
| 6,064,380 A * | 5/2000 | Swenson et al. ............... 715/273 |
| 2003/0014817 A1* | 1/2003 | Gallant et al. ..................... 5/600 |
| 2007/0176920 A1* | 8/2007 | Raijmakers et al. .......... 345/418 |
| 2009/0076856 A1* | 3/2009 | Darby et al. ........................ 705/3 |
| 2010/0084996 A1* | 4/2010 | Van De Sluis et al. ........ 315/312 |
| 2010/0115548 A1* | 5/2010 | Leyvi ............................... 725/34 |
| 2010/0312042 A1* | 12/2010 | Anderson ............. A61M 21/02 600/28 |
| 2011/0137110 A1* | 6/2011 | Aarts et al. ....................... 600/27 |
| 2012/0323090 A1* | 12/2012 | Bechtel et al. ................ 600/306 |
| 2012/0323591 A1* | 12/2012 | Bechtel et al. .................... 705/2 |
| 2013/0212633 A1* | 8/2013 | Emerson et al. .............. 725/106 |

OTHER PUBLICATIONS

Roberts J. Robbins,"Database Fundamentals", 1995, pp. 1-31.*
(Continued)

*Primary Examiner* — Navin Natnithithadha
*Assistant Examiner* — Sunita Reddy
(74) *Attorney, Agent, or Firm* — Jones Day (57) ABSTRACT

The present invention relates to time-driven personalization of media preference. In an embodiment, the present invention includes a therapy for treating altered cognitive states, such as understimulation, overstimulation and sundowning, in individuals suffering from cognitive impairment, including dementia. The present invention uses time to focus its therapies through personal care shows. The time-based personal care shows include personalized content (e.g., images, music, trusted voice) and format (e.g., tempo, length of intervals, color contrast) to ensure effectiveness of the personal care shows in reaching the desired results.

11 Claims, 7 Drawing Sheets

(56) References Cited

OTHER PUBLICATIONS

Baker, Roger, Holloway, Jane, Holtcamp, Chantal, Larsson, Anita, Hartman, Lindy, Pearce, Rebecca, Scherman, Birgitta, Johansson, Seija, Thomas, Peter, Wareing, Lesley Ann, Owens, Matthew; Effects of Multi-Sensory Stimulation for People with Dementia; Journal of Advanced Nursing, 43(50); pp. 465-477; 2003.

Jones, Scott; An Interpersonal Approach to Psychotherapy With Older Persons With Dementia; Professional Psychology: Research and Practice, 26(6); pp. 602-607; 1995.

Smith, Glenn; Sundowning: Late-day Confusion; Mayo Clinic; 2009.

Feinstein, Justin, Duff, Melissa, Tranel, Daniel; Sustained Experience of Emotion After Loss of Memory in Patients with Amnesia; Proceedings of the National Academy of Sciences of the United States of America, 107(17); pp. 7674-7679; 2010.

Yonan, Cynthia, Sommers, Mitchell; The Effects of Talker Familiarity on Spoken Word Identification in Younger and Older Listeners; Psychology and Aging, 15(1); pp. 88-99; 2000.

Gotell, Eva, Brown, Steven, Ekman, Sirkka-Liisa; The Influence of Caregiver Singing and Background Music on Vocally Expressed Emotions and Moods in Dementia Case: A Qualitative Analysis; International Journal of Nursing Studies; 2008.

Ridder, Hanne Melte; Wigram, Tony, Ottesen, Aase Marie; A Pilot Study on the Effects of Music Therapy on Frontotemporal Dementia—Developing a Research Protocol; Nordic Journal of Music Therapy, 18(2); pp. 103-132; 2009.

Cohen, Gillian, Taylor, Stephanie; Forum: Reminiscence and Ageing; Ageing and Society, 18(5); pp. 601-610; 1998.

* cited by examiner

TIME-DRIVEN PERSONALIZATION OF MEDIA PREFERENCE

This application claims priority to U.S. Provisional Patent Application No. 61/568,988, filed Dec. 9, 2011, and entitled "Time-Driven Personalization of Media Preference," the entirety of which is herein incorporated by reference.

FIELD OF THE INVENTION

This invention relates, generally, to media preference over time periods. More particularly, it relates to time-based suggestions, preferences and personalization of various media, including both specific media and format of media.

DESCRIPTION OF THE PRIOR ART

Cognitive wellness in human beings is affected by a plethora of internal and external factors, including, age, intelligence, culture, stress levels, anxiety, nutrition, medication, among others. In turn, cognitive wellness itself can affect performance on various tests, social capacities, basic abilities to function on a daily bases, among others. Therefore, persons with lower cognitive wellness might have lower test scores or difficulties performing basic tasks. These difficulties are further exacerbated in individuals having diminished or declining physical or mental capacities, symptoms that can be found in dementia and other diseases/conditions.

Similarly, an individual can experience various levels of altered cognitive states, wherein the individual does not or cannot maximally process all of the information and stimuli surrounding him/her. An altered cognitive state may cause the individual to become confused, agitated, delusional, etc. A multitude of conditions can cause any type of person to experience an altered cognitive state, from severe dementia to simple medication, among other diseases and circumstances.

Individuals prone to these diminished or declining physical or mental capacities can include the elderly, mentally handicapped individuals, and those who have suffered debilitating injury or disease. These individuals are particularly prone to depression, anxiety, agitation, confusion, etc. brought on by feelings of helplessness and isolation caused by the decline in physical or mental capacities. These feelings of helplessness, confusion and isolation may be caused by understimulation, overstimulation and/or late-day confusion.

Understimulation is a problem for many older adults. It becomes increasingly difficult for these older adults to enjoy the activities that they once enjoyed. Cognitive impairment leads to weakened abilities to process sensory stimuli, which makes normal stimuli confusing (R. Baker, et al., Effects of multi-sensory stimulation for people with dementia, Journal of Advanced Nursing, 43:5, 465-477 (2003). Because the individual cannot process the stimuli or is not provided sufficient stimuli, he/she becomes bored, or understimulated.

Understimulation manifests itself into a variety of behaviors, including crying, yelling, repeating questions, restlessness, wandering and confusion. Relieving understimulation presents many challenges. As dementia progresses, the experiences that normally provided an emotional boost no longer do so. The art has provided no effective treatment for treating understimulation.

Often, pharmaceuticals are used to address the symptoms caused by understimulation. However, using pharmaceuticals with older adults presents several problems. Rather than address the causes of understimulation, pharmaceuticals tend to address the symptoms resulting from understimulation. Thus, the causes remain unaddressed, prompting continued or increased use of the medication. Side effects and adverse reactions to pharmaceuticals are particularly common in older adults, in part because bodies metabolize medications differently as they age.

With possible side effects including sedation, weakness, dizziness, disorientation and depression, the reactions to pharmaceuticals frequently mirror or amplify the symptoms of dementia and related diseases. This complicates treatment and has the potential to accelerate both physical and cognitive decline. The interaction of each additional medication further increases the risk of debilitating side effects.

Overstimulation occurs in an older adult when too much stimuli causes the adult to feel overwhelmed. Overstimulation overwhelms the senses and diminishes the ability to concentrate. As individuals age, they become more sensitive to commotion that, when younger, they could ignore. The stress threshold decreases as individuals lose cognitive ability (S. Jones, Interpersonal approach to psychotherapy with older persons with dementia, Professional Psychology: Research and Practice, 26:6, 602-607 (1995)).

Often the anxiety caused by overstimulation is addressed by pharmaceutical intervention with psychotropic medications. Rather than address the causes of the stress/anxiety, pharmaceuticals tend to subdue the symptoms. The stress triggers remain unaddressed, prompting continued or increased use of the medication. Side effects and adverse reactions to pharmaceuticals are particularly common in older adults taking psychotropic medicine, in part because bodies metabolize medications differently as they age.

With possible side effects including sedation, weakness, dizziness, disorientation and depression, the reactions to psychotropic drugs frequently mirror or amplify the symptoms of dementia and related diseases. This complicates treatment and has the potential to accelerate both physical and cognitive decline. The interaction of each additional medication further increases the risk of debilitating side effects and may lead to the onset of delirium.

Late-day confusion, or sundowning syndrome, is a rapid but temporary decline in cognitive function that occurs each afternoon or evening in many older adults, particularly those with dementia. It is a distinct onset or worsening or several symptoms in the late afternoon or evening. For seniors suffering from a decline in cognitive function due to aging, late days and evenings may bring confusion, increased agitation, disorientation, lack of energy, motor disturbances, emotional distress and/or difficulty communicating.

The art presents no effective treatment of sundowning. Pharmaceutical interventions are rarely effective and often bring debilitating side effects. General reminiscence therapies, while effective during periods of higher functioning, may infuriate or frustrate a person in a sundowning state. Introducing familiar items, such as photographs or familiar items from home, may calm the sundowning individual (Glenn Smith, Sundowning: Lade-day confusion, Mayo Clinic (2009)). However, it is difficult to predict which items will soothe and re-focus the sundowning individual and which will further upset him/her.

A person's mood or mental state can be affected by a variety of daily experiences, from minor experiences, such as receiving an unexpected compliment or finding a great parking spot, to more significant experiences, such as an enlightening conversation with a dear friend. Often, one can trace an unexpectedly good mood back to a seemingly minor experience.

Because certain facts and short-term memories may slip away more easily with advancing age, older adults are sometimes unable to recall what put them in that particular mood, whether positive or negative. However, the emotional impact of that experience endures, regardless of whether the person remembers the experience that led to it. The resultant emotions persist independent of the memory of the experience itself (J. S. Feinstein et al., Sustained experience of emotion after loss of memory in patients with amnesia, Proceedings of the National Academy of Sciences of the United States of America, 107:17, 7674-7679 (2010)). Thus, when a sufferer of dementia is visited by a loved one, that experience typically triggers a positive emotion that will linger even if the patient subsequently does not recall the actual visit of the loved one.

Regardless of short-term memory loss, an older adult's state-of-mind improves after positive experiences. The emotional boost persists after the event that caused it is forgotten (J. S. Feinstein et al., Sustained experience of emotion after loss of memory in patients with amnesia, Proceedings of the National Academy of Sciences of the United States of America, 107:17, 7674-7679 (2010)). The emotional boost may result in a variety of effects, from eating on a regular basis to reduced agitation to better communication. The inability to recall the positive experience (e.g., visit from a loved one) does not diminish the positive impact of the experience itself.

Familiar voices create emotional responses every day, whether over the phone, on the radio or television, or in person. For seniors experiencing a decline in cognitive functioning due to aging, trusted voices have the power to calm, to re-orient, and to reassure. The benefits can be experienced whether the senior is engaged in conversation or is provided simple reassurances.

Even if a resident at a senior housing facility misidentifies a loved one's voice, the resident may still benefit from it. Auditory memories have additional resilience to the effects of aging and dementia (C. A. Yonan et al., Psychology and Aging 2000, 15:1, 88-99 (2000)). A person with dementia is often able to identify a loved one's voice as belonging to someone who they know and trust, even if he/she is unable to define the exact relationship to the speaker.

Problems arise when periods of time, sometimes significant, elapse between a loved one's visits and/or phone calls to a resident. Though the resident may experience an emotional boost during the loved one's visit or phone call, the frequency of receiving this emotional boost is dependent on the loved one. Moreover, if a resident is feeling agitated or confused and thus has an immediate need for an emotional boost but the loved one is unable to visit or call, the resident must handle his/her agitation or confusion without the emotional boost.

Music is another method of providing this emotional boost to seniors suffering from dementia or other cognitive impairment that alters one's cognitive state. Musical memories often last well into advanced age, so familiar songs elicit particular emotions. Background music and singing have been shown to be useful interventions for dementia patients (E. Gotell, Caregiver singing and background music in dementia care, Western Journal of Nursing Research, 23:2, 195-216 (2002)). Additional studies have confirmed that, following music therapy, individuals suffering mental or emotional impairment due to aging display an increase in quality-of-life scores, reduced agitated behaviors, and a decrease in disturbances (H. M. Ridder, A pilot study on the effects of music therapy on frontotemporal dementia—developing a research protocol, Nordic Journal of Music Therapy, 18:2, 103-132 (2009).

Problems may arise if music therapy is performed improperly on a patient, for example when a patient's mood and/or time of day are not considered. In many cases, music therapy can have adverse effects on a patient who is understimulated, overstimulated or sundowning when that patient's understimulation, overstimulation or sundowning is not considered.

Another known therapeutic method for cognitive impairment, or condition that alters one's cognitive state, is reminiscence therapy. This therapy purports to help adults who might experience memory loss, leaving them feeling disconnected or confused. Certain categories of memories react differently to aging. Recent and short-term memories are vulnerable to the damaging effects of aging, while long-term memories are generally more resistant. It is well-established that people with dementia are able to recall more remote (e.g., long-term) memories than short-term memories (G. Cohen et al., Forum: Reminiscence and ageing, Ageing and Society, Vol. 18, 601-610 (1998)). Significant memories from youth create an adult's sense of self, containing his/her earliest experiences that define him/her. For example, memories can include a childhood home, love interests, schooling, summer camps, friends and family, etc. Reminiscence therapy, including showing the adult image reminders of these memories, allows an adult to revisit those memories to reinforce self-identity.

Problems with reminiscence therapy arise, however, when images are depicted at an improper time and thus have an adverse effect on the cognitively-impaired adult. These errors are most common when attempting to reach a certain result, particularly during altered cognitive states, such as understimulation, overstimulation and sundowning. Showing images improperly to a dementia patient might further the patient's symptoms (e.g., stress, anxiety, confusion, etc.) when time of day is not considered.

Other problems that exist with reminiscence therapy and music therapy include the inability to determine which therapies work at particular times of the day. Stimulation and confusion in cognitively-impaired adults, particularly residents in assisted living facilities, generally can be driven by time of day. Playing an improper therapy at a particular time of the day can cause adverse effects. On the other hand, in order to provide significant benefits, such as decreased anxiety and confusion, increased communication, increased energy, etc., utilizing a proper therapy must consider whether the residents are understimulated, overstimulated or sundowning; whether the therapy is appropriate for the particular time of day/week/year; and whether the therapy is aligned with the resident's interests.

Another problem that may exist in particular residents is that caregivers, who speak to confused, anxious or stressed residents in attempt to calm them down, may be construed by the residents as insults. Thus, attempts to calm these residents only serve to further their dementia symptoms.

Accordingly, what is needed is a method of providing therapy to persons with cognitive impairment, wherein the method is results-oriented and is driven by the time of day. However, in view of the art considered as a whole at the time the present invention was made, it was not obvious to those of ordinary skill how said art could be advanced.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

SUMMARY OF THE INVENTION

The long-standing but heretofore unfulfilled need for a non-drug therapeutic for the related treatments of understimulation, overstimulation and sundowning is now met by a new, useful, and nonobvious invention.

A first embodiment of the present invention includes a system for the personalization of media to persons of any emotional state, physical state, cognitive ability, and/or cognitive state based on time.

A separate embodiment of the present invention includes a method of personalizing media to an individual of any emotional state, physical state, and/or cognitive ability based on time.

Another embodiment of the present invention further includes a method of treating understimulation, overstimulation and/or sundowning in individuals with impaired cognitive ability through the personalization of media based on time.

Yet another embodiment of the present invention comprises a computer program product including software executable instructions stored in a computer readable medium for performing a method by running a software program on a computer, the method including issuing instructions from the computer software program comprising the steps for personalizing media to an individual of any emotional state, physical state, and/or cognitive ability based on time. This embodiment further includes steps for treating understimulation, overstimulation and/or sundowning in individuals with impaired cognitive ability through the same personalization of media based on time.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the nature and objects of the invention, reference should be made to the following detailed disclosure, taken in connection with the accompanying drawings, in which.

DETAILED DESCRIPTION OF THE PREFERRED EMBODIMENT

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

Figure 2A:
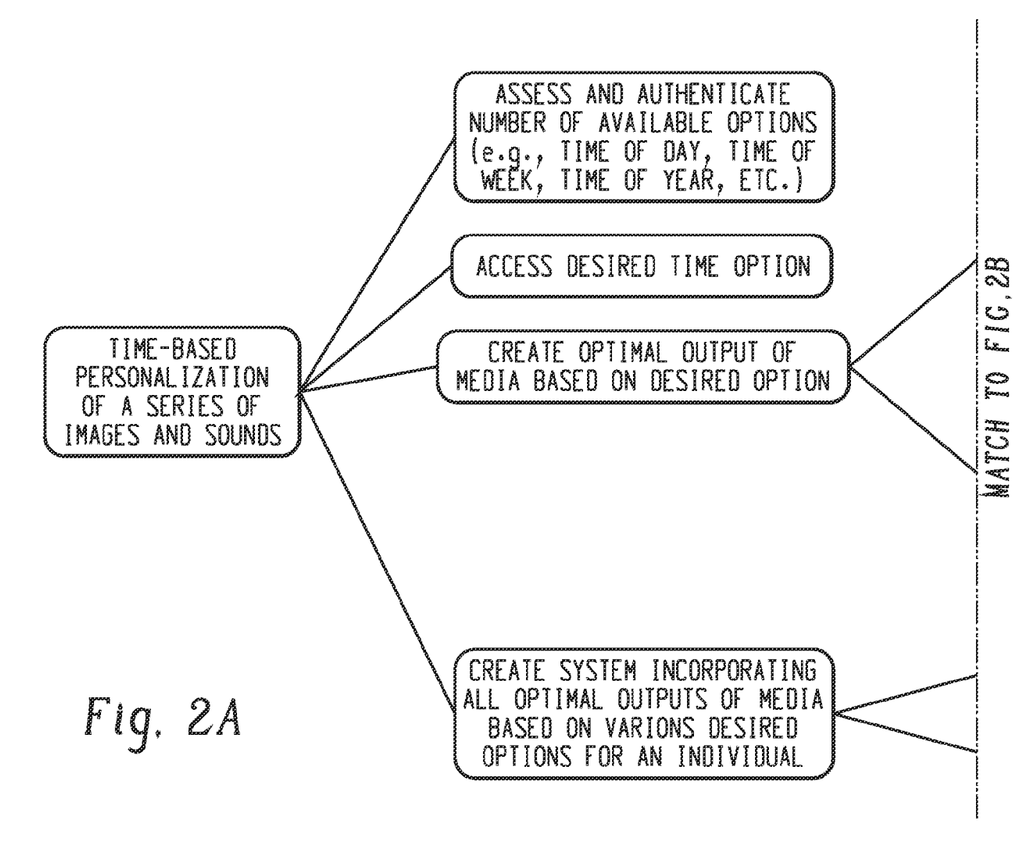
FIGS. 2A and 2B (Collectively FIG. 2) depict an example macro or micro-rating system.
Figure 2B:
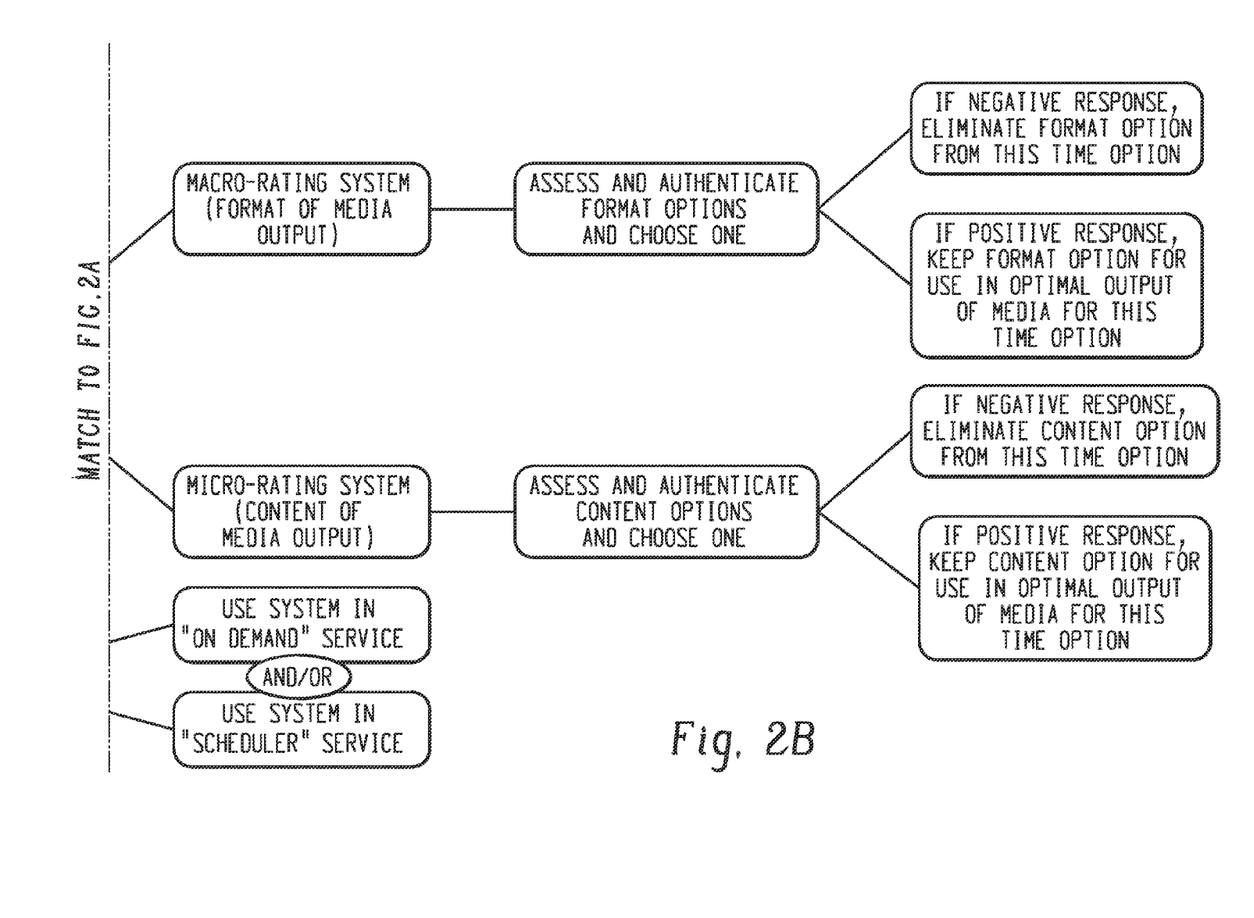

The present disclosure makes reference mainly to persons with cognitive impairment. However, application of certain embodiments of the present invention to persons of any emotional state, physical state, and cognitive ability is contemplated. Generally, as depicted in FIG. 2, the idea is for a system to use time (e.g., time of day, time of week, time of year, etc.) to provide individualized media to any person, the media including both content and format.

I. Understimulation

Understimulation is a problem for many older adults in the midst of cognitive decline. It can show up in a variety of forms, including crying, yelling, repeating questions, restlessness, wandering and/or confusion. As minds and bodies of individuals age, it generally becomes harder and harder to enjoy the activities once enjoyed. Often, memories from earlier in life continue to provide a positive response. Difficulty with short-term memory may lead to boredom and frustration, or understimulation. One of the main effects of aging is that details of short-term memories become difficult to retrieve, while specific life details or time periods from earlier in life remain accessible.

Certain embodiments of the current invention provide a personalized mix of music and images, specific to each resident's level of cognitive functioning. These embodiments can determine which long-term memories provide positive stimulation for residents, so as to offset understimulation during a particular time of day. Using these memories, a personal care show can be created and repeatedly presented to the resident to show the resident pleasant memories of family and friends, places and times. Personal care shows may comprise images, music, trusted voice, or other pieces of similar content with the appropriate format. When a resident is understimulated, the resident needs more active, upbeat content (e.g., images and music) to overcome the understimulation.

These personal care shows may also result in improved cognitive performance, as residents may be informed of upcoming events, reminded of daily tasks and oriented to their surroundings. Thus, the resident can live more independently. Levels of cognitive impairment may vary across residents and severities.

II. Overstimulation

Overstimulation is also a problem for many older adults in the midst of cognitive decline. Overstimulation occurs when chaotic situations overwhelm a resident's senses and lowers the resident's ability to concentrate. As cognitive capacity decreases, the stress threshold is also lowered. This poses problems for residents facing memory challenges. Overstimulation can be manifested in a variety of forms, including anxiety, stress and confusion. The amount of stimulation that residents can comfortably handle varies from resident to resident.

Certain embodiments of the current invention provide a therapy to soothe and relax anxiety caused by overstimulation. By playing personalized images and music at an appropriate volume and tempo at the time of day when the resident is overstimulated, residents are able to control their level of stimulation. Once a resident has fine-tuned their most comfortable level of stimulation, they are free to relax and reengage at their own pace. When a resident is overstimulated, the resident needs calmer images and music to eliminate the overstimulation. The same individual can be both understimulated and overstimulated at different points during the day.

III. Sundowning

Late-day confusion, also known as sundowning or sundowning syndrome, is a problem for many older adults during rapid decline of brain function. Sundowning can manifest itself in various forms, including confusion, agitation, disorientation, roaming, paranoia and hallucinations. Sundowning generally is a temporary condition usually appearing around 4:00 PM to 7:00 PM each afternoon/evening, wherein a resident who is sundowning may exhibit mood swings, become abnormally demanding, suspicious, upset or disoriented, and/or hallucinate. A resident may feel clear and relaxed in the morning but exhibit fear and confusion as the afternoon progresses.

Certain embodiments of the current invention combine images and music that a resident personally finds most comforting and can re-focus the resident to being consciously aware of his/her present environment. Media is presented in a manner and format with an aim to relax and engage the resident. By accessing pleasant therapies and applying them to a distressed resident, stress is reduced and comfort levels heightened.

These embodiments also direct the appropriate content and format at the appropriate time personalized to each resident to reduce stress and confusion. For example, a sundowning resident, who worked as a farmer thirty years earlier, may become confused in the afternoon/evening and believe he must tend to his evening farm chores when in actuality, he lives in an assisted living facility and no longer farms. In this case, an embodiment of the current invention would play images in particular intervals to turn the resident's attention off of farming and onto other hobbies that the resident enjoys more than farming. The embodiment may also play calming music at a particular tempo to reduce the resident's stress level.

In another example, a sundowning resident who believes she should be at her childhood home, rather than the assisted living facility, may be shown a personalized show of her siblings as adults. Once the resident accepts that her siblings are adults, then the resident realizes that she can no longer be living at her childhood home. Again, calming music may be played as well. The format of the images and/or music would be customized to ensure the show's effectiveness in bringing the resident out of her sundowning state.

IV. Disorientation of Place and Time

Validation therapy involves entering a resident's personal reality and meeting them where they are to orient the resident back to the proper time and/or place.

a. Orientation to Place

Validation therapy may be needed to orient a resident to a place when the resident believes he/she is at a location separate from his/her current location. Familiar settings/locations allow residents to feel comfortable and relaxed. Individuals with mild cognitive impairment may become disoriented when faced with an unfamiliar environment, and individuals with dementia may not feel comfortable even in familiar settings.

Certain embodiments of the current invention alleviate this disorientation to space by having a resident undergo a therapy that is spatially and temporally relevant. For example, a resident may be presented with a trusted voice that describes the setting in her room and that assures her that she is safe. This resident may be presented with similarly relevant music as well to calm her. The appropriate images, music, voice recordings, etc. are determined by this embodiment of the current invention by using the proper content and format to achieve the desire result at the right time of day.

b. Orientation to Time

Advancing age may cause one's focus to narrow, permitting one to concentrate only on a single subject at any given moment and limiting one's ability to comprehend the time from one's surroundings. With advancing age, time orientation reminders that once occurred naturally may begin to lose their significance. For example, when one is beginning to struggle with memory difficulties, one may lose the association of the sun setting with the approach of going to bed, or the clue to time is not being processed and/or the clue to time is processed but forgotten within short-term memory.

Often, cognitively-impaired residents feel suspicion that they should be doing something else at a given time. The resident may feel as though something is left undone but cannot recall what it is. Disorientation to time may manifest itself as anxiety or distress.

Certain embodiments of the current invention establish time-driven cues to orient residents to the time of day, week, and/or year. For example, a resident who no longer understands when dinner is served may be shown images of dinner items and soft music to orient him to time and upcoming events. The images shown and music played would be based on this embodiment's ability to transform the resident's ratings of the variables (i.e., content+format) to produce an effective personal care show therapy.

An example of a cue orienting a resident to time of the week can include cuing for religious services on Sunday, football on Monday, and/or any event that may occur regularly or irregularly in the resident's weekly schedule. An example of a cue orienting a resident to time of the year can include cuing for the holidays in December, birthdays, summer season, and/or any event that may occur regularly or irregularly in the resident's yearly schedule.

V. Rating

Certain embodiments also provide for a macro-rating system and/or a micro-rating system, as depicted in FIG. 2. A macro-rating system is directed to the format of media output, the format including, but not limited to, tempo of music, volume of music, number of times a trusted voice (i.e., familiar voice that calms the resident) is played, time interval length for images, among any other attributes of format of media. A micro-rating system is directed to the content of the media output, the content including, but not limited to, the images shown, brightness of images, contrast of images, music played, and familiar voices heard, among any other attributes of content of media.

When determining therapy for altered cognitive states, such as understimulation, overstimulation and sundowning, the time of day is considered. With understimulated residents, shows are generally time-sensitive for format. With overstimulated residents, shows are generally time-sensitive for format. With sundowning, shows are generally time-sensitive for content. Time-sensitivity for content may include time of day, time of week and/or time of year.

A resident, caregiver or system itself might use the macro-rating system to change or adapt the format of the shows to the personal needs of the resident. A resident, caregiver or system itself might use the micro-rating system to change or adapt the content of the shows to the personal needs of the resident. Each therapy can be optimized for time-sensitivity of format and content, such that a resident has therapies when experiencing an altered cognitive state, such as overstimulation, understimulation and/or sundowning. Whether a resident needs more stimulation, less stimulation or sundowning direction in relation to time can determine the construction of each show. The therapies are driven by results and time-sensitivity, so if a particular therapy is not working at a particular time of day, the micro-rating system and macro-rating system can change or adapt the format and content of the therapy to be more effective for the resident.

VI. Example 1

Figure 3A:
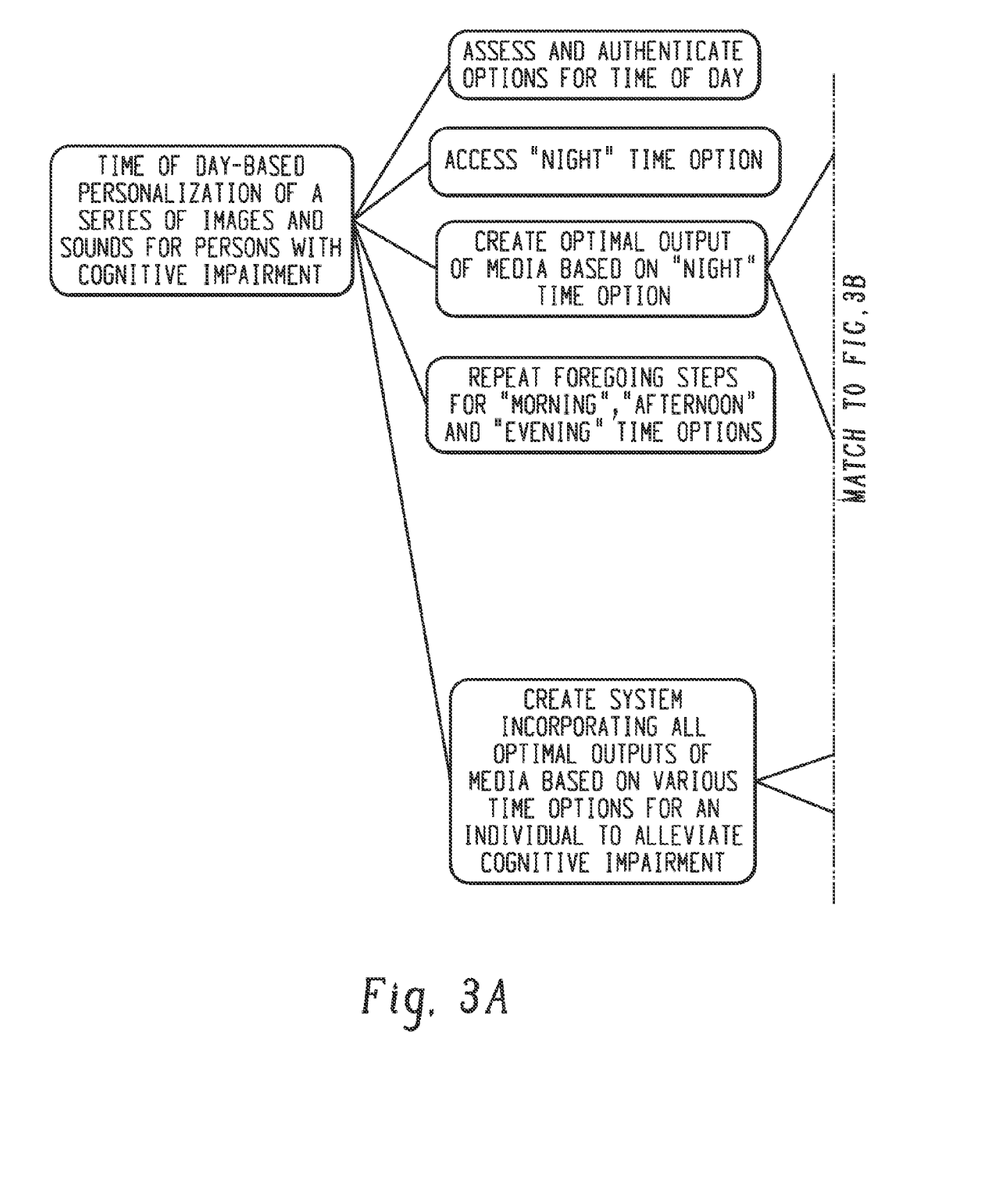
FIGS. 3A, 3B, and 3C (Collectively FIG. 3) depict another example macro or micro-rating system.
Figure 3B:
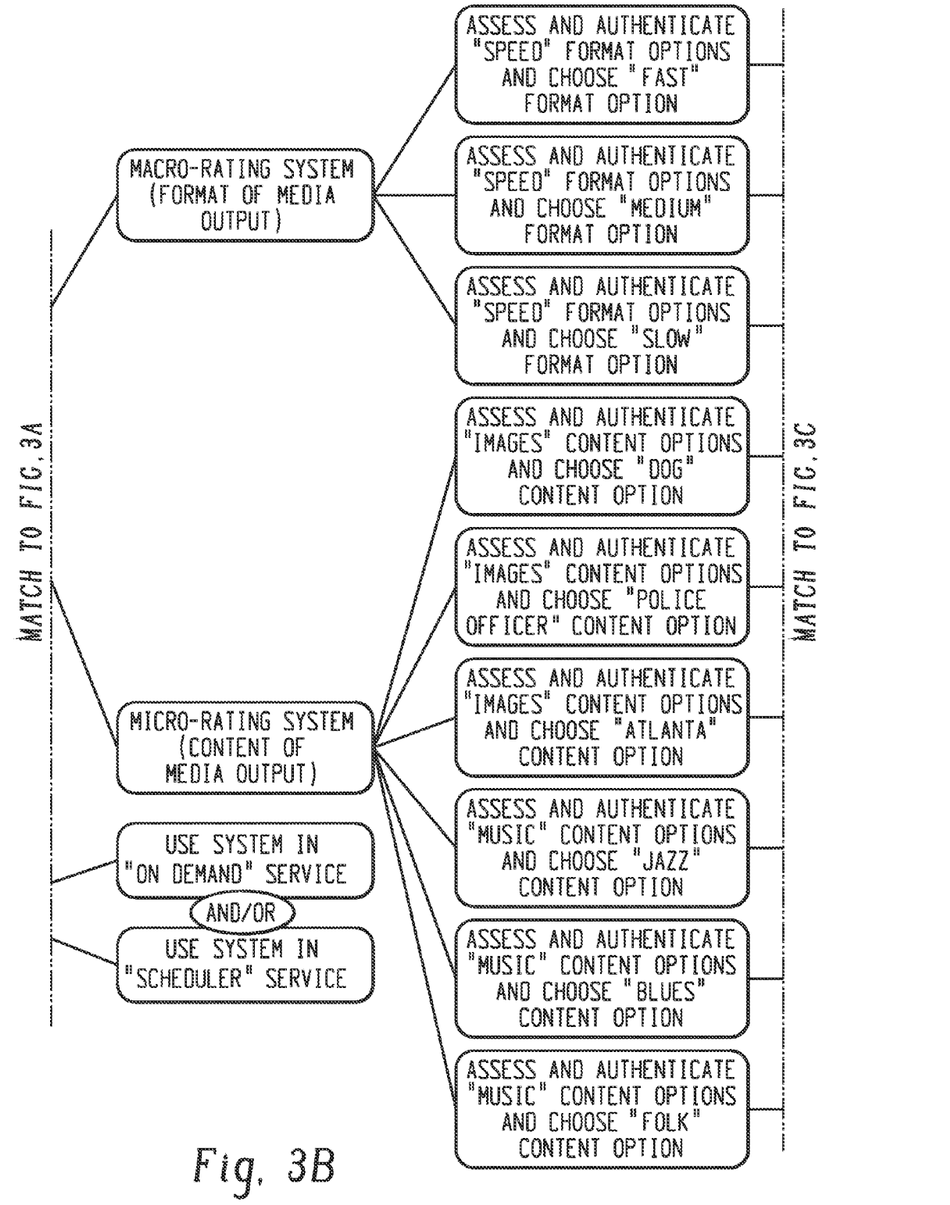
Figure 3C:
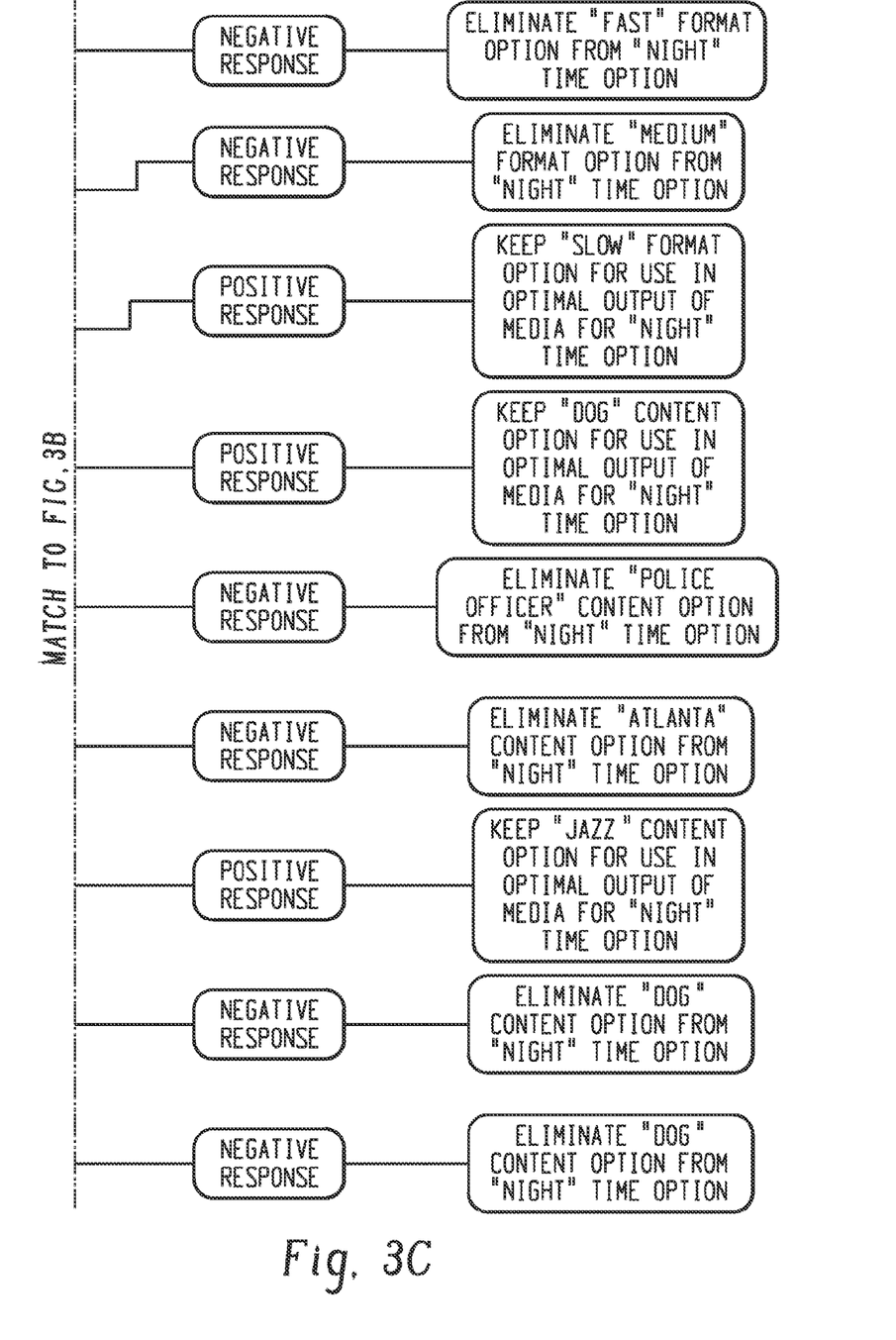

In one embodiment, as depicted in FIG. 3, three variables are presented—media, format and time of day. Media comprises individual pieces of media, including, for example as here, image and genre of music (depicted in Table 1 as A, B, C, D, E, G). Format comprises three options—fast, medium or slow (depicted in Table 2 as F, M, S, respectively). Format includes length of time image is on the screen and tempo of music in this embodiment but can include other considerations, such as number of trusted voice recordings played or color contrast of image. Time of day may include any categories of time but in this embodiment comprises 8:00 PM to 6:00 AM as "night," 6:00 AM to noon as "Morning," noon to 4:00 PM as "afternoon," and 4:00 PM to 8:00 PM as "evening."

|  | Media | | | | | |
|---|---|---|---|---|---|---|
|  | Images | | | Music | | |
| Time | A (dog) | B (police officer) | C (Atlanta) | D (jazz) | E (blues) | G (folk) |
| Night | Y | N | N | Y | N | N |
| Morning | Y | Y | N | Y | N | N |
| Afternoon | Y | N | N | Y | N | Y |
| Evening | Y | N | N | Y | N | Y |

Table 1 depicts an example of a resident's positive engagement for various media or content. The symbol "Y" indicates a positive engagement with the content. The symbol "N" indicates a non-positive engagement with the content.

Table 1 depicts an example of a resident's positive engagement for various media or content, in this case dogs, former occupation as a police officer, the city of Atlanta, jazz music, blues music and folk music. The term "positive engagement" is used herein to refer to a resident's enjoyment of particular content and/or format, which tends to have a positive effect on the resident's mood, for example reducing confusion, reducing stress levels, increasing communication, increasing calmness, etc.

Positive engagement can be measured by a resident's level of engagement (i.e., the micro-rating system) to each element of media at each time of day. The resident is seen to have a positive engagement for dogs at all times. The resident is seen to have an positive engagement for his former occupation as a police officer in the early morning time period. The resident is seen to have no positive engagement for the city of Atlanta at any time. The resident is seen to have a positive engagement for jazz music at all times. The resident is seen to have no positive engagement for blues music at any time. The resident is seen to have an positive engagement for folk music during mid-day, afternoon and evening time periods. These results are due to the effects of this resident undergoing different cognitive states, for example sundowning at different times of the day and night, and thus needing particular content at those times.

The macro-rating system determines the overall effect of a show, for example images with dogs combined with jazz music from Table 1, with each format. In Table 2, "Fast" is defined as five (5) seconds per image of dog and greater than 160 beats per second of jazz music; "Medium" is defined as six (6) to 119 seconds per image of dog and 159 to 41 bears per second of jazz music; "Slow" is defined as 120 seconds per image of dog and less than sixty (40) beats per second of jazz music.

|  | Format | | |
|---|---|---|---|
| Time | Fast (F) | Medium (M) | Slow (S) |
| Night | N | N | Y |
| Morning | Y | Y | N |
| Afternoon | Y | Y | N |
| Evening | N | N | Y |

Table 2 depicts an example of a resident's positive engagement for format of media. The symbol "Y" indicates a positive engagement for the format. The symbol "N" indicates a non-positive engagement with the format.

Table 2 depicts how formats can be changed and personalized to each resident. In this embodiment, the resident has an positive engagement for a fast format in the early morning and afternoon; for a medium format in the early morning, mid-day and afternoon; and a slow format for night, mid-day and night. These results are due to the effects of this resident undergoing an altered cognitive state, such as understimulation, overstimulation or sundowning, at different times of the day and night and thus needing particular format at those times.

The resident may or may not know what the various formats utilized are. For example, this procedure may use metatags to recognize that the resident needs a slower tempo at a particular time of day based on the micro-rating system, and automatically slow the tempo of the music. The resident himself/herself or a resident proxy may alter the format as well.

When Table 1 and Table 2 are combined resulting in Table 3, the resident receives therapies that are personalized to that resident at particular times of the day and night. According to Tables 1 and 2, the resident will experience positive effects with the following combinations during the listed time categories:

| Time | Media | Format |
|---|---|---|
| Night | A, D | S |
| Morning | A, B, D | F, M |
| Afternoon | A, D, G | F, M |
| Evening | A, D, G | S |

Table 3 depicts an example of a resident's positive engagement for content and format, resulting from the findings of Tables 1 and 2.

Combining content and format in this manner creates a rule set that is used to help residents cope with their altered cognitive states on a daily basis during particular time periods. Other types of content include, but are not limited to, familiar voice recordings, and other types of format, such as the time format (e.g., different categories, time of the week or year, etc.) or color contrast of images. This content can be utilized using a substantially similar procedure as described to create the personalized therapies.

VII. Example 2

An embodiment of the current invention provides an "on demand" service, wherein a user, caregiver, etc. chooses an option that media is needed. The media is then outputted by this embodiment in the appropriate content and format based on time, whether it is time of the day, time of the month, time of the year, etc.

Because the device outputs a proper content and format of media, the caregiver, for example, who determines that some form of media is needed, is not required to know which altered cognitive state the resident is experiencing, whether it is understimulation, overstimulation, sundowning, or none. The caregiver need only know that the media is needed.

For example, using Table 3 from Example 1, if a resident becomes visibly upset in the morning time, the caregiver may simply choose an option that media is needed. This particular device may then know to output media with a content of "police officer" and "jazz," and a format of "fast." The caregiver need only determine that media is needed.

VIII. Example 3

An embodiment of the current invention provides a "scheduler" service, wherein media is preset for particular times of the day/month/year. This embodiment requires the caregiver only to determine that media is needed at a particular predetermined time, and the device implements the proper content and format of the media.

For example, if a resident typically sundowns at 7:30 PM, his particular device may be preset to show media at 7:30 PM. The device may then determine the proper format and content of media to bring the resident out of his sundowning state.

The idea generally is that this embodiment does not provide just a pure cue for a particular event, but it connects the media with the event or activity. Thus, it is personalized for each user.

IX. Implementation

Figure 1A:
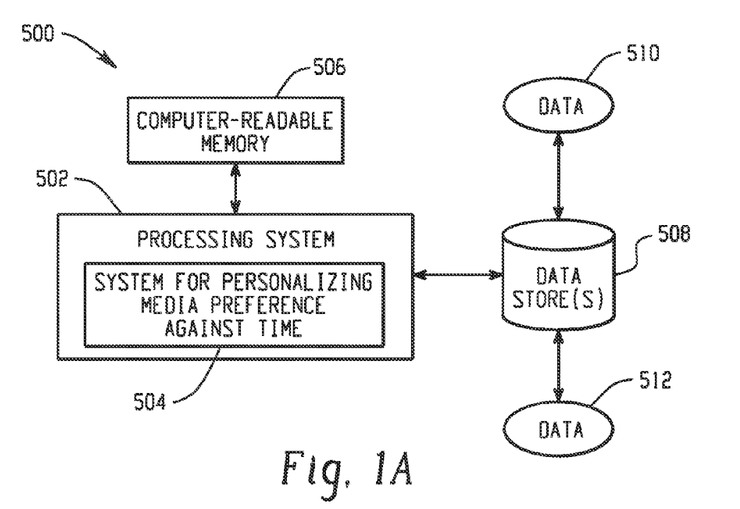
FIGS. 1A, 1B, and 1C depict example systems for use in implementing time-driven relief of cognitive impairment.
Figure 1B:
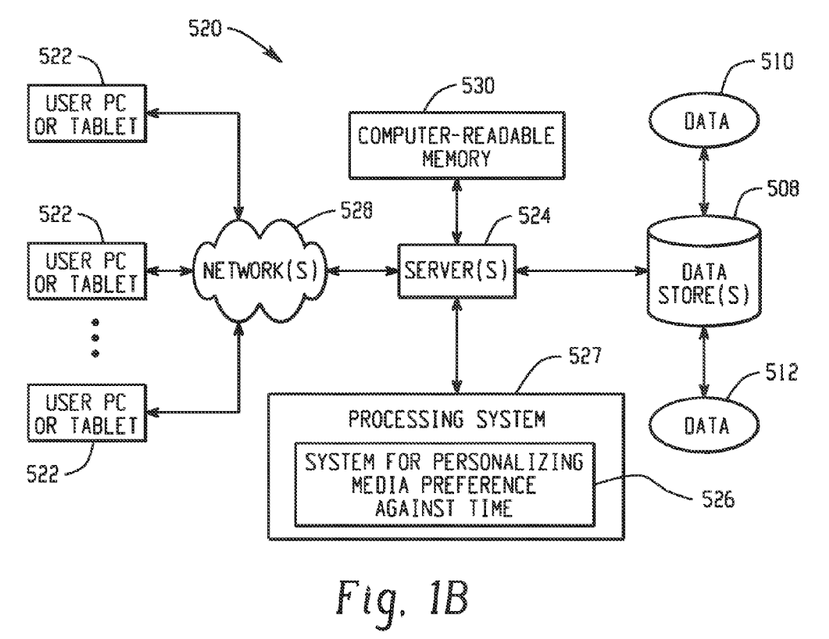
Figure 1C:
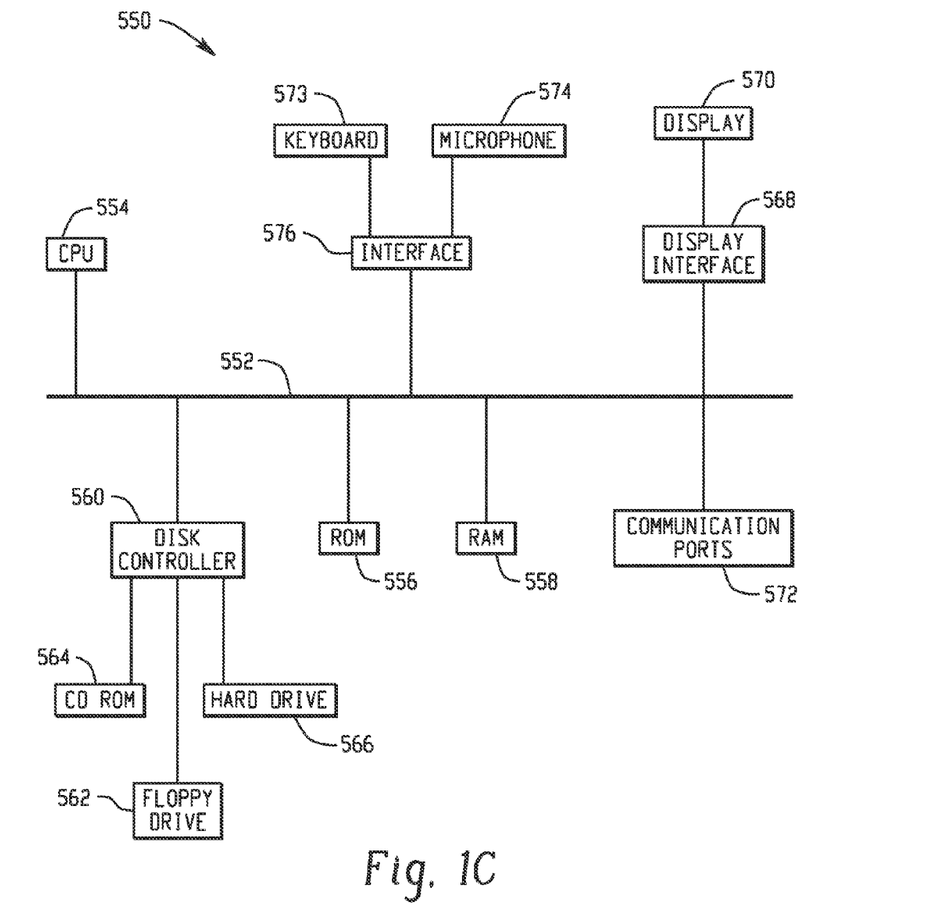

FIGS. 1A, 1B, and 1C depict example systems for use in implementing a time-driven analyzer of media preference. For example, FIG. 1A depicts an exemplary system 500 that includes a standalone computer architecture where a processing system 502 (e.g., one or more computer processors) includes a time-driven analyzer of media preference 504 being executed on it. The processing system 502 has access to a computer-readable memory 506 in addition to one or more data stores 508. The one or more data stores 508 may include a variety of data 510, 512.

FIG. 1B depicts a system 520 that includes a client server architecture. One or more user PCs or tablets 522 accesses one or more servers 524 running a time-driven analyzer of media preference 526 on a processing system 527 via one or more networks 528. The one or more servers 524 may access a computer readable memory 530 as well as one or more data stores 532. The one or more data stores 532 a variety of data 534, 536.

FIG. 1C shows a block diagram of exemplary hardware for a standalone computer architecture 550, such as the architecture depicted in FIG. 1A that may be used to contain and/or implement the program instructions of system embodiments of the present invention. A bus 552 may serve as the information highway interconnecting the other illustrated components of the hardware. A processing system 554 labeled CPU (central processing unit) (e.g., one or more computer processors), may perform calculations and logic operations required to execute a program. A processor-readable storage medium, such as read only memory (ROM) 556 and random access memory (RAM) 558, may be in communication with the processing system 554 and may contain one or more programming instructions implementing a time-driven analyzer of media preference. Optionally, program instructions may be stored on a computer readable storage medium such as a magnetic disk, optical disk, recordable memory device, flash memory, or other physical storage medium. Computer instructions may also be communicated via a communications signal, or a modulated carrier wave.

A disk controller 560 interfaces one or more optional disk drives to the system bus 552. These disk drives may be external or internal floppy disk drives such as 562, external or internal CD-ROM, CD-R, CD-RW or DVD drives such as 564, or external or internal hard drives 566. As indicated previously, these various disk drives and disk controllers are optional devices.

Each of the element managers, real-time data buffer, conveyors, file input processor, database index shared access memory loader, reference data buffer and data managers may include a software application stored in one or more of the disk drives connected to the disk controller 560, the ROM 556 and/or the RAM 558. Preferably, the processor 554 may access each component as required.

A display interface 568 may permit information from the bus 556 to be displayed on a display 570 in audio, graphic, or alphanumeric format. Communication with external devices may optionally occur using various communication ports 572.

In addition to the standard computer-type components, the hardware may also include data input devices, such as a keyboard 572, or other input device 574, such as a microphone, remote control, pointer, mouse and/or joystick.

As additional examples, for example, the systems and methods may include data signals conveyed via networks (e.g., local area network, wide area network, internet, combinations thereof, etc.), fiber optic medium, carrier waves, wireless networks, etc. for communication with one or more data processing devices. The data signals can carry any or all of the data disclosed herein that is provided to or from a device.

Additionally, the methods and systems described herein may be implemented on many different types of processing devices by program code comprising program instructions that are executable by the device processing subsystem. The software program instructions may include source code, object code, machine code, or any other stored data that is operable to cause a processing system to perform the methods and operations described herein. Other implementations may also be used, however, such as firmware or even appropriately designed hardware configured to carry out the methods and systems described herein.

The systems' and methods' data (e.g., associations, mappings, data input, data output, intermediate data results, final data results, etc.) may be stored and implemented in one or more different types of computer-implemented data stores, such as different types of storage devices and programming constructs (e.g., RAM, ROM, FLASH memory, flat files, databases, programming data structures, programming variables, IF-THEN (or similar type) statement constructs, etc.). It is noted that data structures describe formats for use in organizing and storing data in databases, programs, memory, or other computer-readable media for use by a computer program.

The computer components, software modules, functions, data stores and data structures described herein may be connected directly or indirectly to each other in order to allow the flow of data needed for their operations. It is also noted that a module or processor includes but is not limited to a unit of code that performs a software operation, and can be implemented for example as a subroutine unit of code, or as a software function unit of code, or as an object (as in an object-oriented paradigm), or as an applet, or in a computer script language, or as another type of computer code. The software components and/or functionality may be located on a single computer or distributed across multiple computers depending upon the situation at hand.

It will thus be seen that the objects set forth above, and those made apparent from the foregoing disclosure, are efficiently attained. Since certain changes may be made in the above construction without departing from the scope of the invention, it is intended that all matters contained in the foregoing disclosure or shown in the accompanying drawings shall be interpreted as illustrative and not in a limiting sense.

It should be understood that as used in the description herein and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise. Finally, as used in the description herein and throughout the claims that follow, the meanings of "and" and "or" include both the conjunctive and disjunctive and may be used interchangeably unless the context expressly dictates otherwise; the phrase "exclusive or" may be used to indicate situation where only the disjunctive meaning may apply.

It is also to be understood that the following claims are intended to cover all of the generic and specific features of the invention herein described, and all statements of the scope of the invention that, as a matter of language, might be said to fall therebetween.

What is claimed is:

1. A method of providing non-drug therapy for treatment of understimulation, overstimulation, or sundowning by presenting wirelessly transmitted personalized media, that is adjusted over time based on symptoms of an individual, to the individual on a tablet user interface device, comprising the steps of:
using a processing system:
determining one or more future times for which media shows are to be presented to the individual on the tablet user interface device;
generating a media show for a particular future time of the one or more future times for which media shows are to be presented by:
accessing presentation parameters for the particular future time, wherein the presentation parameters are accessed based on the particular future time, the presentation parameters being generated and adjusted by a data model that combines data from a media content data structure and a media format data structure to maintain a presentation by time of day data structure from which the presentation parameters are obtained;
accessing a plurality of media content items, each media content item being associated with one or more media content parameters indicated in the presentation by time of day data structure, each media content item being associated with a media type;
creating the media show based on the presentation parameters indicated in the presentation by time of day data structure, the media content parameters, and a macro-rating system and a micro-rating system,
the macro-rating system identifying a format of a target media show by specifying types of content that will appear in the target media show at different times in the target media show, and
the micro-rating system identifying content of the target media show by specifying a list of media content items that are presentable in the target media show;
wherein the target media show is created by, for each of the different times of the target media show:
determining a specific type of content that will appear in the target media show based on data from the media content data structure that is augmented by the macro-rating system;
selecting a specific media content item for that different time of the target media show by searching the plurality of media content items for one or more media content items that match the specific type of content and are on the list, augmented by the micro-rating system, of media content items that are presentable;
repeating the foregoing steps for each of the other one or more future times;
wirelessly transmitting the media show to the tablet user interface device;
automatically playing the media show using the tablet user interface device upon a determination that a current time is the particular future time; and
receiving feedback via the macro-rating system and the micro-rating system based on the symptoms of the individual that indicate whether the media show had a desired therapeutic effect on the individual, wherein the media show is adjusted based on the feedback by augmenting values of the media content data structure and the media format data structure by providing the feedback based on the symptoms of the individual to the data model which automatically updates the presentation by time of day data structure to modify the media show for when the media show is played again for the individual in the future.

2. The method of claim 1, wherein the particular future time is a time of day, time of week, time of month, or time of year.

3. The method of claim 1, wherein the particular future time is a time of day selected from the group consisting of night, morning, afternoon, and evening.

4. The method of claim 1, wherein the media content parameters identify a category of images that is acceptable for display at the particular future time.

5. The method of claim 1, wherein the media content parameters identify a category of music that is acceptable for playing at the particular future time.

6. The method of claim 1, wherein the media content parameters identify a person whose voice that is acceptable for playing at the particular future time.

7. The method of claim 1, further comprising playing the media show using the tablet user interface device upon receipt of a request from the individual or a caregiver of the individual.

8. The method of claim 1, further comprising scheduling playing of different media shows at each of the one or more future times.

9. The method of claim 1, wherein the received feedback enables continued adjustment of the media show as behavior of the individual changes.

10. A computer implemented system for providing the non-drug therapy for the treatment of the understimulation, the overstimulation, or the sundowning by presenting the wirelessly transmitted personalized media, the media being adjusted over time based on the symptoms of the individual, to the individual on the tablet user interface device, comprising:

the processing system;

one or more computer-readable memories encoded with instructions for commanding the processing system to execute the method of claim 1.

11. A non-transitory computer-readable medium encoded with instructions for commanding the processing system to execute the method of claim 1 for providing the non-drug therapy for the treatment of the understimulation, the overstimulation, or the sundowning by presenting the wirelessly transmitted personalized media, the media being adjusted over time based on the symptoms of the individual, to the individual on the tablet user interface device.

\* \* \* \* \*